United States Patent
Zanella et al.

(10) Patent No.: US 10,695,387 B2
(45) Date of Patent: Jun. 30, 2020

(54) EXTRACTS OF MICROALGAE AND PLANTS FOR REGULATING SEBUM PRODUCTION

(71) Applicant: Cutech SRL, Padua (IT)

(72) Inventors: Lorenzo Zanella, Venezla-Maestre (IT); Paolo Pertile, San Pietro Viminario (IT); Michele Massironi, Padua (IT)

(73) Assignee: Symrise AG, Holzminden (DE)

( * ) Notice: Subject to any disclaimer, the term of this patent is extended or adjusted under 35 U.S.C. 154(b) by 423 days.

(21) Appl. No.: 15/501,628

(22) PCT Filed: Aug. 3, 2015

(86) PCT No.: PCT/EP2015/067860
§ 371 (c)(1),
(2) Date: Feb. 3, 2017

(87) PCT Pub. No.: WO2016/020339
PCT Pub. Date: Feb. 11, 2016

(65) Prior Publication Data
US 2017/0224751 A1    Aug. 10, 2017

(30) Foreign Application Priority Data

Aug. 5, 2014  (EP) .................................... 14179936

(51) Int. Cl.
| | |
|---|---|
| *A61K 36/02* | (2006.01) |
| *A61K 36/185* | (2006.01) |
| *A61K 36/21* | (2006.01) |
| *A61K 36/23* | (2006.01) |
| *A61K 36/28* | (2006.01) |
| *A61Q 5/00* | (2006.01) |
| *A61Q 19/00* | (2006.01) |
| *A61K 8/97* | (2017.01) |
| *A61K 8/9706* | (2017.01) |

(52) U.S. Cl.
CPC ................ *A61K 36/02* (2013.01); *A61K 8/97* (2013.01); *A61K 8/9706* (2017.08); *A61K 36/185* (2013.01); *A61K 36/21* (2013.01); *A61K 36/23* (2013.01); *A61K 36/28* (2013.01); *A61Q 5/006* (2013.01); *A61Q 19/005* (2013.01); *A61Q 19/008* (2013.01); *A61K 2236/00* (2013.01)

(58) Field of Classification Search
None
See application file for complete search history.

(56) References Cited

U.S. PATENT DOCUMENTS

| | | |
|---|---|---|
| 8,591,912 B1 | 11/2013 | Kadam et al. |
| 2014/0010838 A1 | 1/2014 | Zanella et al. |

FOREIGN PATENT DOCUMENTS

| | | | | |
|---|---|---|---|---|
| FR | 2980698 A1 * | 4/2013 | ............. | A61K 36/03 |
| WO | WO-2012052356 A2 * | 4/2012 | ............... | A61Q 5/00 |
| WO | 2015/084136 A1 | 6/2015 | | |

OTHER PUBLICATIONS

Kim et al, "Prospective of the Cosmeceuticals Derived from Marine Organisms," Biotechnol. Bioprocess Eng. 13, Jan. 1, 2008, pp. 511-523.

* cited by examiner

*Primary Examiner* — Susan Hoffman
(74) *Attorney, Agent, or Firm* — Dilworth & Barrese, LLP

(57) ABSTRACT

New extracts of microalgae, halophytes and psammophilous plants are suggested, obtainable by treating said microalgae and plants with a solvent selected from the group consisting of $C_1$-$C_4$ aliphatic alcohols, ethyl acetate, water or their mixtures, removing the dissolved extracts from the residues and recovering the pure extracts from the solvent. The extracts show excellent activity as regulators of the metabolism of human sebaceous glands.

5 Claims, No Drawings

EXTRACTS OF MICROALGAE AND PLANTS FOR REGULATING SEBUM PRODUCTION

FIELD OF INVENTION

The present invention relates to the area of cosmetics and toiletries and refers to extracts obtained from microalgae, halophytes living in salt marshes and psammophilous plants living in coastal sand dunes. The invention also concerns processes and compositions for obtaining said extracts, and their use in hair and skin care applications.

STATE OF THE ART

Throughout the last decades, the cosmetics and toiletry industry has dedicated increasing attention to in the identification of natural compounds suitable for use in the preparation of body care products. The active ingredients extracted from natural organisms, especially if obtained with environmentally-friendly methods and without impacting the wild flora and fauna, have represented the higher growth trend in the cosmetics sector for at least 10 years.

This is due to the increased sensibility of consumers to the ethics of the green economy, especially in the field of voluptuary goods, but also to the awareness that nature houses countless substances with extraordinary beneficial properties, still largely unexploited. Knowledge of natural remedies has been part of the popular culture for centuries but, in the present time founded on science and technology, this heritage has been almost completely forgotten. However, the concept that nature provides cures and therapies promoting the natural defenses of our body is deeply inscribed in our awareness. The present invention is aimed to provide concrete responses to this request for natural products by the cosmetics producers and consumers.

The growth of the market focused on natural active ingredients has also allowed the differentiation of at least two relevant sub-sectors:
- the natural cosmetic products, having formulations based on one or more natural ingredient,
- organic products, i.e. products certified as obtained from compounds and by means of production systems that fully comply with specific international regulations which govern the "organic" label.

Research in the field of active ingredients of natural origin is therefore a very relevant and strategic aspect of the production chain, since it provides new compounds and widens the market for the cosmetics industry, while promoting "sustainable development" that reconciles economic progress with the social responsibility of preserving the planet's equilibrium.

Plants are the main source of natural active ingredients, on a quantitative basis, with particular reference to antioxidants, vitamins and micronutrients. Many of these active compounds have been shown to protect the body from aging processes and environmental damage. Cosmetics have always exploited many natural ingredients obtained from herbs traditionally known for their beneficial effects, as well as extracts from fruits and vegetables cultivated for food. However, more recently, many new plants have been introduced in cosmetics as potential sources of natural active ingredients. In this respect, traditional Chinese medicine has proved an important source of inspiration for researchers.

The present invention is the result of a great research effort aimed to discover innovative natural ingredients or extracts suitable to offer natural and safe solutions to some of the skin problems mentioned hereinafter. Some plant and microalgae extracts have unexpectedly disclosed relevant potential as regulators of the sebaceous gland metabolism. The results reported here were obtained screening all the preparations by means of an innovative ex-vivo culture of human sebaceous glands (DE 102013015560.6; Symrise GMBH & Co. KG & Cutech Srl). The screening methods usually adopted by cosmetics companies are based on immortalized lines of sebocytes, which cannot realistically reproduce the complex functionality of the complete sebaceous gland. Therefore, since the data reported hereinafter were obtained by treating ex-vivo cultures of human glands, they have to be regarded as the more reliable ones presently achievable with preclinical tests.

Sebaceous glands are microscopic exocrine glands found throughout all areas of the skin except the palms of the hands and soles of the feet. They secret a natural oil, called sebum, which participates with the sweat to compose the hydrolipidic film that covers the skin. Human sebum is a complex mixture of triglycerides, fatty acids, wax esters, sterol esters, cholesterol, cholesterol esters and squalene. Sebum is involved in epidermal development and barrier maintenance, transporting antioxidants, contributing to mechanical protection, body odor, and generation of pheromones. Sebum is directly involved in hormonal signaling, epidermal differentiation, and protection from ultraviolet (UV) radiation. It cooperates to reduce skin water loss and modulates composition and proliferation of the natural micro-flora of the skin.

There are two types of sebaceous glands, those connected to hair follicles, in pilosebaceous units, and those that exist independently. When they are associated to the hair follicles, one or more glands may surround each hair follicle, and the glands themselves are surrounded by arrector pili muscles. Sebaceous glands are also found in hairless areas (glabrous skin) of the eyelids (called meibomian glands), nose, penis, labia minora, the inner mucosa of the cheek (Fordyce spots), and nipples.

The overproduction of sebum by sebaceous glands of the scalp is the cause of greasy hair, which is considered a significant aesthetic problem. Many cosmetic treatments, in the form of medicated shampoos and lotions, are proposed to calm the scalp's overproduction of sebum. However, cosmetics companies continuously seek new products, especially if obtained from natural ingredients. The seborrhea is involved in the occurrence of dandruff, a disorder of the scalp characterized by patches of abundant and loosely adherent flakes, usually accompanied by itching. This accentuated desquamation of the scalp can evolve into seborrheic dermatitis, which is a severe form of dandruff accompanied by inflammation and erythema. The etiology of dandruff and seborrheic dermatitis appears to be dependent upon three factors: sebaceous gland secretions, micro-flora metabolism, and individual susceptibility. The regulation of sebum production is therefore a pivotal issue for the prevention of dandruff and seborrheic dermatitis, and the present invention is related with this problem, among others.

Undesirable hyperactivity of sebaceous glands can also occur in other parts of the body, especially on the face. Here the overproduction of sebum gives the skin a shiny and aesthetically undesirable appearance (oily skin) and can promote other slight blemishes, such as comedones. In some cases, more serious disorders can occur in the presence of excessive sebum, such as acne, a skin disease characterized by an inflammatory process of the hair follicle and annexed sebaceous gland. *Propionibacterium acnes* is considered to be the infectious agent in acne.

*P. acnes* are aerotolerant anaerobic bacteria that live deep within follicles and pores, using sebum, cellular debris and metabolic byproducts from the surrounding skin tissue as their primary sources of energy and nutrients. Elevated production of sebum by hyperactive sebaceous glands or blockage of the follicle can favour *P. acnes* bacteria proliferation, causing the inflamed pustules (pimples) characteristic of acne. As a consequence, the cosmetics industry is strongly interested in acquiring compounds suitable to inhibit sebum production, especially if this activity is combined with antinflammatory properties.

Finally, compounds suitable to regulate sebum production can also find application in products for intimate hygiene, since the female external genitals have many sebaceous glands. Mons pubis, labia majora, labia minora and the external side of the vaginal vestibule are rich in sebaceous glands and their sebum secretion interacts with the bacterial microflora, regulating the pH of the genital area. The fresh sebum does not contain significant quantities of free fatty acids, but these are released as an effect of the lipases produced by bacteria, inducing the acidification of the genital environment. The regulation of sebum can therefore represent an important condition for preventing alterations of the genital microflora, irritations, itching, etc.

The present invention is the result of a significant effort to investigate microalgae strains suitable to be cultivated in photobioreactors, and plants living in extreme environments, such as halophytes occurring in salt marshes and psammophilous plants growing on sand dunes of coastal environments.

The plants living in extreme habitats have developed adaptive metabolites to allow the survival in hostile or stressful conditions. The halophytes living in salt marshes, for instance, must tolerate high levels of salt in the soil and frequent submersion by the sea tides. The psammophilous plants, on the other hand, need to comply with a very dry, nutrient poor and instable soil. The wind action continuously modifies the profile of the ground, also producing an erosive effect on everything that protrudes above its surface. Psammophilous plants have therefore developed physiological adaptations and protective metabolites suitable to survive arid conditions, intense solar radiation, high temperature and abrasion effects due to drifting sand.

Plants growing in salt marshes have already occasionally attracted the attention of cosmetics companies, and some data related to their exploitation for skin-care products can be found in the prior art. More than twenty years ago, FR 2657011 B1 (Secma) claimed the use of *Inula* and *Salicornia* for cosmetic and pharmaceutical preparations with anti-radical and antioxidant properties. JP 2010013373 A (Pola Chem Ind. Inc.) refers to preparations obtained from some Chenopodiaceae, among which the halophyte *Salicornia europea*, for modulating the horny layer of skin in order to improve skin barrier functions. Similarly, JP 2005145878 A (Kyoei Chemical Ind. & Kyoei Kagaku Kogyo KK) discloses skin barrier function restorative/antioxidant/anti-inflammatory properties for extracts obtainable from herbs of the genus *Salicornia*. The far eastern halophyte *Salicornia herbacea* was extracted for preparing skin moisturizing products (KR 20020027834 A; Ae Kyung Ind. Co. Ltd.) with anti-wrinkle activity (KR 20110013812 A; Thefaceshop Co. Ltd.) and slimming compositions (KR 20120086438 A, Cosmecca Korea Co. Ltd.).

Less common is the use of psammophilous herbs occurring in marine environment as a source of active ingredients for cosmetics. FR2793682 B1 (Pierre Fabre Dermo-Cosmetique) suggested the use of *Cakile maritima* extracts, a semi-succulent plant on sand dunes and beaches, as an ingredient for dermal-cosmetic products and disclosed some exemplificative procedures of extraction. However, this invention focuses on the biological activity as moisturizer, while there is no reference to the potential activity of the extracts on the human sebaceous glands. In fact, the whole prior art concerning the herbs that are the subject of the present invention is totally silent on the use of their extracts for the regulation of sebum production.

Among the natural organisms of great interest and only recently discovered by cosmetics, the microalgae occupy a prominent place. The biodiversity of microalgae is very high and in great part still uncertain: to date about 35,000 species of microalgae have been described but the number of unknown species is estimated to vary from 200,000 to 800,000. The adaptability of these organisms allows them to synthesize rare and biologically active compounds suitable to sustain specific and diversified environmental stresses or to compete successfully with other organisms. For instance, many species synthesize complex molecules with antibiotic and anticancer properties, some of which have been chemically characterized.

The prior art related to the microalgae exploitation in the field of cosmetics offers several examples, but very few with regard to the application proposed here. The anti-free-radical activity of liquid extracts obtainable from Chlorophyceae, Prasinophyceae, Cryptophyceae, Bacillariophyceae (or diatoms) and Prymnesiophyceae was disclosed in FR 2657012 B1 (Secma) in 1990. The exploitability of *Chaetoceros* for cosmetics products has been known since 1975 thanks to GB 1392131 A (Aubert et al.). Japanese patent JP 3-822959 B2 (Noevir K K) refers to skin lotions effective in preventing skin wrinkles comprising an extract of certain diatoms, particularly *Chaetoceros*. The extraction solvent is selected from ethanol, methanol, 1,3-butylene glycol, water and is used in a single form or a two or more mixed form. In a preferred formulation, these solvents include an inorganic salt and a surfactant. U.S. Pat. No. 5,767,095 (Photonz) discloses topical anti-inflammatory compositions comprising monogalactosyl-dieicosapentanoyl glycerol obtained from *Chaetoceros* and *Thalassiosira*, among others. According to EP 1808483 A1 (Cognis) *Chlorococcum citriforme* has been considered an interesting source of lutein for cosmetic applications. International patent application WO 1997/034489 A1 (Aquaculture Technology) refers to the use of extracts obtained from the marine algae *Chaetoceros* or *Thalassiosira* as anti-bacterially active agents and to compositions containing such agents for use against pathogenic bacteria. International patent application WO 2010/0029115 A1 (LVHM Recherche) proposes the use of certain plant extracts and the microalgae *Thalassiosira*, for reducing skin and hair pigmentation.

The FR 2894473 A1 (Daniel Jouvance) discloses the use of preparations obtained from some microalgae (*Chromulina, Asterionella* and *Tetraselmis*) for inhibiting the enzymes involved in the metabolism of fatty acids and lipids. Slimming preparations from several species of microalgae are proposed in the Japanese patent JP 2000072642 A1 (Lion). For the microalgae considered here, several cosmetic applications focused on hair-care, skin-care, antiaging, modulation of skin melanogenesis and subcutis lipogenesis were disclosed by EP 2629753 A2 (Cutech). The only invention related with the modulation of sebum production is FR 2980698 A1 (Gelyma), which refers to the regulation of sebum production obtained exploiting the combined activity of extracts from the microalga *Tetraselmis chui* and the macroalga *Fucus spiralis*.

However, nothing is reported in the prior art on the biological properties of the plants and microalgae considered here as modulators of sebum production.

DESCRIPTION OF THE INVENTION

In a first embodiment the present invention relates to extracts of microalgae or halophytes or psammophilous plants obtainable by treating said microalgae or plants with a solvent selected from the group consisting of $C_1$-$C_4$ aliphatic alcohols, ethyl acetate, water or their mixtures, removing the dissolved extracts from the residues and recovering the pure extracts from the solvent.

In a second embodiment the present invention also covers a method for obtaining extracts of microalgae or halophytes or psammophilous plants comprising the following steps:
(a) contacting said plant material, optionally minced or crushed or micronized with a solvent selected from the group consisting of $C_1$-$C_4$ aliphatic alcohols, ethyl acetate, water or their mixtures in an amount suitable to effect that the actives move into the solvent phase, optionally at elevated temperatures,
(b) removing the dissolved extract from the residue, and
(c) recovering the pure extract from the solvent.

The research conducted unexpectedly revealed that some extract preparations obtained from different plants and microalgae can be exploited to regulate the sebum synthesis in human sebaceous glands, without exerting any toxic effect. In particular, the object of the present invention was to develop new extracts for cosmetic and, respectively, dermatological applications for the regulation of sebum production containing:

lipophilic and hydrophilic extracts obtained from microalgae belonging to the genus *Chlorococcum*;
lipophilic and hydrophilic extracts obtained from microalgae belonging to the genus *Chaetoceros*;
lipophilic and hydrophilic extracts obtained from microalgae belonging to the genus *Monodus*;
lipophilic and hydrophilic extracts obtained from microalgae belonging to the genus *Thalassiosira*;
lipophilic and hydrophilic extracts obtained from halophytes belonging to the genus *Sarcocornia*;
lipophilic and hydrophilic extracts obtained from halophytes belonging to the genus *Salicornia*;
lipophilic and hydrophilic extracts obtained from psammophilous plants belonging to the genus *Inula*;
lipophilic and hydrophilic extracts obtained from psammophilous plants belonging to the genus *Echinophora*.

*Chaetoceros* sp.

*Chaetoceros*, belonging to the class of Bacillophyceae, is probably the largest genus of marine plankton, more particularly diatoms with approximately 400 species described. Although a large number of these descriptions are no longer valid. It is often very difficult to distinguish between different *Chaetoceros* species. Several attempts have been made to restructure this large genus into subgenera and this work is still in progress. However, most of the effort to describe species has been focused on boreal areas, and the genus is cosmopolitan, so there are probably a large number of tropical species still undescribed. The following compilation illustrates suitable strains of *Chaetoceros* with respect to the present invention: *Chaetoceros abnormis, Chaetoceros aculeatus, Chaetoceros adelianus, Chaetoceros aduncus, Chaetoceros aequatorialis* var. *antarcticus, Chaetoceros aequatorialis, Chaetoceros affinis* f. *pseudosymmetricus, Chaetoceros affinis* f. *parallelus, Chaetoceros affinis* f. *inaequalis, Chaetoceros affinis, Chaetoceros amanita, Chaetoceros anastomosans, Chaetoceros angularis, Chaetoceros angulatus, Chaetoceros anostomosans* var. *speciosus, Chaetoceros armatus, Chaetoceros astrabadicus, Chaetoceros atlanticus* var. *cornpactus, Chaetoceros atlanticus* var. *neapolitanus, Chaetoceros atlanticus* var. *tumescens, Chaetoceros atlanticus, Chaetoceros atlanticus* f. *audax, Chaetoceros atlanticus* var. *cruciatus, Chaetoceros audax, Chaetoceros bacteriastrius, Chaetoceros bacteriastroides* f. *imbricatus, Chaetoceros bacteriastroides, Chaetoceros bermejense, Chaetoceros bisetaceus, Chaetoceros borealis, Chaetoceros borealoides, Chaetoceros breve, Chaetoceros brevis, Chaetoceros brussilowi, Chaetoceros buceros, Chaetoceros buceros, Chaetoceros bulbosus, Chaetoceros bulbosus* f. *cruciatus, Chaetoceros bulbosus* f. *schimperana, Chaetoceros bungei, Chaetoceros calcitrans* f. *pumilus, Chaetoceros californicus, Chaetoceros capense, Chaetoceros caspicus, Chaetoceros caspicus* var. *karianus, Chaetoceros caspicus* f. *pinguichaetus, Chaetoceros castracanei, Chaetoceros castracanei, Chaetoceros ceratospermus* var. *minor, Chaetoceros ceratosporus* var. *brachysetus, Chaetoceros ceratosporus, Chaetoceros chunii, Chaetoceros cinctus, Chaetoceros clavigera, Chaetoceros clavigerus, Chaetoceros clevei, Chaetoceros coarctatus, Chaetoceros cochleus, Chaetoceros cornpactus, Chaetoceros cornpressus* var. *gracilis, Chaetoceros cornpressus* var. *hirtisetus, Chaetoceros concavicorne, Chaetoceros confervoides, Chaetoceros confusus, Chaetoceros constrictus, Chaetoceros convolutus, Chaetoceros convolutus* f. *trisetosus, Chaetoceros convolutus* f. *volans, Chaetoceros cornutus, Chaetoceros coronatus, Chaetoceros costatus, Chaetoceros crenatus, Chaetoceros crinitus, Chaetoceros criophilus, Chaetoceros cruciatus, Chaetoceros curvatus, Chaetoceros curvisetus, Chaetoceros dadayi, Chaetoceros danicus, Chaetoceros debilis, Chaetoceros decipiens* f. *singularis, Chaetoceros decipiens, Chaetoceros delicatulus, Chaetoceros densus, Chaetoceros diadema, Chaetoceros dichaeta* f. *unicellularis, Chaetoceros dichaetus, Chaetoceros dichaetus* var. *polygonus, Chaetoceros didymus* var. *praelongus, Chaetoceros didymus* f. *aestivus, Chaetoceros didymus* f. *autumnalis, Chaetoceros didymus, Chaetoceros difficilis, Chaetoceros distichus, Chaetoceros distinguendus, Chaetoceros diversicurvatus, Chaetoceros diversus* var. *mediterraneus, Chaetoceros diversus, Chaetoceros eibenii, Chaetoceros elmorei, Chaetoceros elongatus Chaetoceros exospermus, Chaetoceros externus, Chaetoceros fallax, Chaetoceros femur, Chaetoceros filiferus, Chaetoceros filiforme, Chaetoceros flexuosus, Chaetoceros fragilis Chaetoceros furca* var. *macroceras, Chaetoceros furcellatus, Chaetoceros fusus, Chaetoceros galvestonense, Chaetoceros gastridius, Chaetoceros gaussii, Chaetoceros glacialis, Chaetoceros glandazii, Chaetoceros gobii, Chaetoceros gracilis, Chaetoceros grunowii, Chaetoceros hendeyi, Chaetoceros hispidus* var. *monicae, Chaetoceros hohnii, Chaetoceros holsaticus, Chaetoceros ikari, Chaetoceros imbricatus, Chaetoceros incurvus* var. *umbonatus, Chaetoceros incurvus, Chaetoceros indicus, Chaetoceros ingolfianus, Chaetoceros intermedius, Chaetoceros karianus, Chaetoceros karyanus, Chaetoceros knipowitschii, Chaetoceros laciniosus, Chaetoceros laciniosus* f. *protuberans, Chaetoceros laciniosus* f. *pelagicus, Chaetoceros lauderi, Chaetoceros leve, Chaetoceros littorale litorale, Chaetoceros lorenzianus* var. *forceps, Chaetoceros lorenzianus, Chaetoceros malygini, Chaetoceros medius, Chaetoceros meridiana, Chaetoceros mertensii, Chaetoceros messanense, Chaetoceros minimus, Chaetoceros misumensis,*

*Chaetoceros mitra, Chaetoceros muelleri* var. *duplex, Chaetoceros muelleri* var. *subsalsum, Chaetoceros muelleri, Chaetoceros muellerii* var. *subsalsus, Chaetoceros nansenii, Chaetoceros natatus, Chaetoceros neglectus, Chaetoceros neobulbosus, Chaetoceros neocompactus, Chaetoceros neogracile, Chaetoceros neupokojewii, Chaetoceros nipponicus, Chaetoceros odontella, Chaetoceros okamurae* var. *tetrasetus, Chaetoceros okamurae, Chaetoceros ostenfeldii, Chaetoceros pachtussowii, Chaetoceros pachyceros, Chaetoceros pacificus, Chaetoceros paradoxus, Chaetoceros paradoxus* var. *luedersii, Chaetoceros parvus, Chaetoceros paulsenii* f. *robustus, Chaetoceros pavillardii, Chaetoceros pelagicus, Chaetoceros pendulus, Chaetoceros perpusillus, Chaetoceros peruvianus* var. *victoriae, Chaetoceros peruvianus* var. *gracilis, Chaetoceros peruvianus, Chaetoceros peruvianus* var. *robustum, Chaetoceros peruvianus* var. *suadivae, Chaetoceros peruvianus* f. *volans, Chaetoceros peruvianus* f. *robustus, Chaetoceros phuketensis, Chaetoceros pingue, Chaetoceros pinguichaetus, Chaetoceros pliocenus, Chaetoceros protuberans, Chaetoceros pseudoaurivillii, Chaetoceros pseudocrinitus, Chaetoceros pseudocurvisetus, Chaetoceros pseudodichaeta, Chaetoceros pundulus, Chaetoceros radians Chaetoceros radicans, Chaetoceros recurvatus* f. *robustus, Chaetoceros recurvatus, Chaetoceros robustus, Chaetoceros rostratus, Chaetoceros russanowi, Chaetoceros salsugineus, Chaetoceros saltans, Chaetoceros schmidtii, Chaetoceros schuettii* f. *oceanicus, Chaetoceros secundus, Chaetoceros seiracanthus, Chaetoceros sessile, Chaetoceros setoense, Chaetoceros seychellarus, Chaetoceros seychellarus* var. *austral, Chaetoceros siamense, Chaetoceros similis, Chaetoceros simplex, Chaetoceros skeleton, Chaetoceros socialis* f. *radians, Chaetoceros socialis, Chaetoceros socialis* var. *autumnalis, Chaetoceros sedowii, Chaetoceros strictus, Chaetoceros subcompressus, Chaetoceros subsalsus, Chaetoceros subsecundus, Chaetoceros subtilis, Chaetoceros sumatranus, Chaetoceros tenuissimus, Chaetoceros teres* f. *spinulosus, Chaetoceros teres, Chaetoceros tetrachaeta, Chaetoceros tetras, Chaetoceros tetrastichon, Chaetoceros thienemannii, Chaetoceros throndsenii* var. *trisetosus, Chaetoceros throndsenii* var. *throndsenia, Chaetoceros throndsenii, Chaetoceros tortissimus, Chaetoceros transisetus, Chaetoceros vanheurckii, Chaetoceros vermiculus, Chaetoceros villosus, Chaetoceros vistulae, Chaetoceros volans, Chaetoceros weissflogii, Chaetoceros wighamii, Chaetoceros willei, Chaetoceros zachariasi* var. *longus, Chaetoceros zachariasii* var. *variatus, Chaetoceros zachariasii* var. *lotus, Chaetoceros zachariasii* and *Chaetoceros ziwolkii.*

The preferred strain selected for the present invention is *Chaetoceros calcitrans* f. *pumilus,* a marine strain isolated in 1960 from marine waters at Urayasu (Chiba Prefecture, Japan) near Umbayashi. This latter one is archived as strain CCAP 1010/11 at the Culture Collection of Algae and Protozoa (CCAP) managed by the Scottish Association for Marine Science (also registered in other collections as PLY537; CCMP1315; NEPCC 590).

*Thalassiosira* sp.

Among the various strains of *Thalassiosira,* also belonging to the class of Bacillariophyceae, *Thalassiosira pseudonana* is the best known species of marine centric diatom. It was chosen as the first eukaryotic marine phytoplankton for whole genome sequencing. *T. pseudonana* was selected for this study because it is a model for diatom physiology studies, belongs to a genus widely distributed throughout the world's oceans, and has a relatively small genome at 34 mega base pairs. In particular the strain CS173 obtainable from the Australian CSIRO collection (also registered as CCMP1335 at Provasoli-Guillard National Centre for Culture of Marine; NEPCC58 at the Canadian Centre for the Culture of Microorganisms) is preferably used. This clone was originally collected in 1958 from Moriches Bay (Long Island, N.Y.) and has been maintained continuously in culture.

*Thalassiosira weissflogii* is a large diatom (6-20 μm×8-15 μm) that is used in the shrimp and shellfish larviculture industry. This alga is considered by several hatcheries to be the single best algae for larval shrimp. The cell size is 16 fold the biomass of *Chaetoceros* and 3 fold the biomass of *Tetraselmis.* During the winter this algae is about 15 microns, but shrinks to about 5 microns during the summer. The color of TW varies from brown to green to yellow, depending on the amount of chlorophyll in the culture. This color change does not in any way affect the quality of the algae.

Other strains of interest for and suitable to be considered as source of biological material for the present invention include the following: *Thalassiosira* aff. *antarctica, Thalassiosira antarctica, Thalassiosira decipiens, Thalassiosira eccentrica, Thalassiosira floridana, Thalassiosira gravida, Thalassiosira guillardii, Thalassiosira hyalina, Thalassiosira minima, Thalassiosira nordenskioeldii, Thalassiosira oceanica, Thalassiosira oestrupii, Thalassiosira punctigera, Thalassiosira rotula* and *Thalassiosira tumida.* All these strains of *Thalassiosira* are suitable as starting materials in order to obtain the extracts according to the present invention.

*Monodus* sp.

*Monodus* sp., belonging to the class Eustigmatophyceae, is a class of microalgae rich in polyunsaturated fatty acids. The preferred strain is *Monodus subterraneus* (also known as *Monodus. subterranea*) and in particular the strain CCAP 848/1 obtainable from the Culture Collection of Algae and Protozoa managed by the Scottish Association for Marine Science (also registered as ATCC 30593; UTEX 151 and SAG 848-1) is preferably used.

Other strains of interest for and suitable to be considered as source of biological material for the present invention include the following: *Monodus subterranea majus, Monodus acuminata, Monodus amicimei, Monodus chodatii, Monodus coccomyxa, Monodus coccomyxoides, Monodus cystiformis, Monodus fusiformis, Monodus guttula, Monodus pyreniger, Monodus subglobosa, Monodus subsalsus* and *Monodus unipapilla.*

*Chlorococcum* sp.

*Chlorococcum* is a genus of algae, in the Chlorococcaceae family. The following compilation illustrates suitable strains of *Chlorococcum* with respect to the present invention: *Chlorococcum acidum, Chlorococcum aegyptiacum, Chlorococcum botryoides, Chlorococcum choloepodis, Chlorococcum citriforme, Chlorococcum costatozygotum, Chlorococcum diplobionticum, Chlorococcum dissectum, Chlorococcum echinozygotum, Chlorococcum elbense, Chlorococcum elkhartiense, Chlorococcum ellipsoideum, Chlorococcum hypnosporum, Chlorococcum infusionum, Chlorococcum isabeliense, Chlorococcum lobatum, Chlorococcum macrostigmatum, Chlorococcum minimum, Chlorococcum minutum, Chlorococcum novaeangliae, Chlorococcum oleofaciens, Chlorococcum olivaceum, Chlorococcum pamirum, Chlorococcum pinguideum, Chlorococcum polymorphum, Chlorococcum pseudodictyosphaerium, Chlorococcum pyrenoidosum, Chlorococcum refringens, Chlorococcum salinum, Chlorococcum schizochlamys,*

*Chlorococcum schwarzii, Chlorococcum submarinum, Chlorococcum tatrense* and *Chlorococcum vacuolatum*.

The preferred strain selected for the present invention is *Chlorococcum minutum*, archived as strain CCAP 213/7 (SAG 213-7; SAG 21.95; UTEX 117; CCAO 290) at the Culture Collection of Algae and Protozoa (CCAP) managed by the Scottish Association for Marine Science. This latter was isolated by Bold from soil in India.

*Salicornia* sp.

*Salicornia* is a widely distributed salt-marsh plant with fleshy scalelike leaves, belonging to the Chenopodiaceae family (or Amaranthaceae according to an alternative taxonomical classification). It is also known by the popular name "glasswort" because in medieval and early post-medieval times the ashes of the burned plant were exploited in glassmaking due to their high alkali content.

Many species of *Salicornia* can be used as an ingredient for the present invention, however, the preferred species are *Salicornia europaea* (common glasswort) and *Salicornia veneta*, endemic to the North Adriatic and very common in the lagoon of Venice. *Salicornia* is highly edible, either cooked or raw. Other species suitable to be exploited as material source for the present invention are: *Salicornia bigelovii* (dwarf glasswort), *Salicornia depressa, Salicornia dolichostachya, Salicornia emerici, Salicornia herbacea, Salicornia maritima* (slender glasswort), *Salicornia nitens, Salicornia obscura, Salicornia patula, Salicornia prostrata, Salicornia pusilla, Salicornia ramosissima* (purple glasswort) and *Salicornia rubra*.

The genus *Salicornia* and the following genus *Sarcocornia* comprise very homogeneous species from a morphological, ecological and systematic point of view. They are expected to show similar biological properties also for the applications proposed here.

*Sarcocornia* sp.

This plant is very similar to the previous one and both are generally grouped under the name glasswort. However, the genus *Sarcocornia* comprises perennial halophytes occurring in middle and high tidal marsh zones, salt or brackish marshes; also diked nontidal seasonal saline wetlands. *Sarcocornia* was formed from species formerly belonging to *Salicornia* and *Arthrocnemum*, however, the taxonomy of this genus is difficult and specialists have no a univocal interpretation.

The preferred species for preparing the extracts object of this invention is *Sarcocornia fruticosa*, however, many other species can be considered as source of biological material for the present invention. These include: *Sarcocornia alpini, Sarcocornia ambigua, Sarcocornia blackiana* (thick-head glasswort), *Sarcocornia capensis, Sarcocornia decumbens, Sarcocornia globosa, Sarcocornia littorea, Sarcocornia magellanica, Sarcocornia mossiana, Sarcocornia natalensis, Sarcocornia neei, Sarcocornia obclavata, Sarcocornia pacifica* (=*Salicornia virginica*) (Pacific swampfire, Pacific glasswort), *Sarcocornia perennis* (chickenclaws, perennial glasswort, Virginia glasswort), *Sarcocornia pillansii, Sarcocornia pulvinata, Sarcocornia quinqueflora* (Australian samphire), *Sarcocornia quinqueflora* ssp. *quinqueflora, Sarcocornia quinqueflora* ssp. *tasmanica, Sarcocornia terminalis, Sarcocornia utahensis* (Utah swampfire) and *Sarcocornia xerophila*.

*Inula* sp.

*Inula* is a large genus of about 90 species of flowering plants in the Asteraceae family, many of which are commonly cultivated as garden flowers. *Inula* (=*Limbarda*) *crithmoides*, also known as golden samphire, is a Eurasian perennial coastal species, which may be found growing on sea-cliff ledges, salt marshes or coastal sandy beaches and dunes. Young leaves may be eaten raw or cooked as a leaf vegetable. It is very tolerant to salt, and can grow on light (sandy), medium (loamy) and heavy (clay) soils, however, it prefers well-drained soil. It shows a bushy habit and has semi-succulent leaves.

*Inula crithmoides* is the preferred species for the present invention, however, other species can be considered as source of biological material for the present invention, including the following: *Inula acaulis* (stemless *inula*), *Inula acervata, Inula acinacifolia, Inula acuminata, Inula afghanica, Inula anatolica, Inula auriculata, Inula bifrons, Inula britannica* (British yellowhead), *Inula candida, Inula cappa, Inula caspica, Inula clarkei, Inula conyzae, Inula cuspidata, Inula ensifolia, Inula eupatorioides, Inula falconeri, Inula forrestii, Inula germanica, Inula grandis, Inula helenioides, Inula helenium, Inula helianthus-aquatica, Inula helvetica, Inula hirta, Inula hookeri, Inula hupehensis, Inula japonica, Inula koelzii, Inula lineariifolia, Inula magnifica, Inula montana, Inula multicaulis, Inula nervosa, Inula obtusifolia, Inula oculus-christi, Inula orientalis, Inula pterocaula, Inula racemosa, Inula rhizocephala, Inula rhizocephaloides, Inula rubricaulis, Inula salicina* (Irish fleabane, willowleaf yellowhead), *Inula salsoloides, Inula sericophylla, Inula spiraeifolia, Inula stewartii, Inula subfloccosa, Inula thapsoides, Inula verbascifolia* and *Inula wissmanniana*.

*Echinophora* sp.

This genus belongs to the Apiaceae family (or Umbelliferae) and comprises several species occurring in coastal sandy environments. Some species are known for their therapeutic properties, e.g. *E. platyloba* occurring in Iran. *Echinophora sibthorpiana* or *Echinophora tenuifolia* are sometimes used as a flavoring in tarhana, a middle-eastern dish based on a fermented mixture of grains and yoghurt or fermented milk.

The species of most interest for the present invention is *E. spinosa*, a perennial semi-succulent herb up to 60-70 cm tall, growing on coastal sand dunes of the Mediterranean. The aerial part dies in winter, but the underground rhizome survives, developing up to 1 m in length. Stems are erect, robust and branched, grayish-green in color. The leaves are sparse and rigid, deeply divided in stingray lobes, inferiorly keeled, terminating with a pungent rigid spine. The inflorescence has 6-10 rays and is positioned at the top of the stem.

However, other species can be considered as potential source of biological material for the present invention: *Echinophora carvifolia, Echinophora chrysantha, Echinophora cinerea, Echinophora lamondiana, Echinophora orientalis, Echinophora platyloba, Echinophora scabra, Echinophora tenuifolia, Echinophora tournefortii* and *Echinophora trichophylla*.

Extraction Process of Microalgae

Another object of the present invention relates to a process for obtaining the extracts adopted for the experimental activities. The microalgal biomass can be obtained by cultivation in photobioreactors or in large polyethylene bags or tanks, under daylight or artificial light. The cultivation can occur indoors or outdoors. Some microalgal strains can be also cultivated in heterotrophic conditions, in the dark, in appropriate bioreactors.

When the microalgal biomass reaches a suitable cell density, it can be harvested by centrifugation or sedimentation or flocculation or with other techniques suitable to preserve the integrity of the cell material. The harvested biomass is freeze dried and packaged in vacuum sealed plastic bags or aluminum foil bags, then frozen and preserved at −20° C. till the time of extraction.

Basically, the extracts according to the present invention may be prepared by methods known per se, for example, by aqueous, organic or aqueous/organic extraction of the microalgae using the solvents explained hereinafter. Suitable extraction processes are any conventional extraction processes such as maceration, re-maceration, digestion, agitation maceration, vortex extraction, ultrasonic extraction, counter current extraction, percolation, re-percolation, evacolation (extraction under reduced pressure), diacolation and solid/liquid extraction under continuous reflux. Percolation is advantageous for industrial uses. Any size reduction methods known to the expert, for example, freeze grinding, may be used. Preferred solvents for the extraction process are methanol, ethanol, isopropyl alcohol, ethyl acetate, hexane and water (preferably hot water with a temperature above 80° C., and more particularly above 95° C.) or mixtures of said organic solvents and water, more particularly, low molecular weight alcohols with more or less high water contents. An extraction with methanol, ethanol and water-containing mixtures thereof is particularly preferred. The extraction process is generally carried out at temperatures of from about 10 to about 100° C. In one preferred embodiment, the extraction process is carried out in an inert gas atmosphere to avoid the oxidation of the ingredients of the extract. This is particularly important where extraction is carried out at temperatures above 40° C. The extraction times are selected by the expert depending on the starting material, the extraction process, the extraction temperature, and the ratio of solvent to raw material, etc. After the extraction process, the crude extracts obtained may optionally be subjected to other typical steps, such as, for example, purification, concentration and/or decoloration. If desired, the extracts thus prepared may be subjected, for example, to the selective removal of individually unwanted ingredients. The extraction process may be carried out to any degree, but is usually continued to exhaustion. Typical yields (=extract dry matter based on the quantity of raw material used) in the extraction of the starting materials are of the order of from about 1 to about 50%, preferably from about 2 to about 20%, and more preferably from about 5 to about 15% b.w.—calculated on the starting materials.

In the following, the typical process for obtaining the microalgae extracts according to the invention is described in more detail:

Each gram of dry biomass was extracted by treatment with 100 ml of solvent, stirring the suspension at room temperature for 16 hours in the dark;

the residual cell material was separated from the extract by centrifugation at 2000 G for 15 minutes;

the residual biomass was washed by suspending it in 50 ml of solvent;

the cell material was separated from the washing solvent by centrifugation at 2000 G for 15 minutes;

the residual biomass was washed again by suspending it in 50 ml of solvent;

the cell material was separated from the washing solvent by centrifugation at 2000 G for 15 minutes;

the firstly collected extract and the washing solvent volumes were mixed, and the resulting extract was considered to have a conventional concentration of 5000 µg/ml (1000 mg of dry algae in 200 ml of solvent).

According to the present invention, cell material of the aforementioned microalgae was extracted with a liquid extractant selected from the group consisting of ethyl acetate, isopropanol, ethanol, methanol and water.

The extractant can also comprise a mixture of two or more of the aforementioned solvents. Hereinafter, the microalgae extract concentrations will be conventionally expressed as the ratio between the quantity (in weight) of cell material treated and the extractive solvent (in volume). For instance, by treating 1 g of dry powered microalgae with 200 ml of extractive solvent, 200 ml of extract at 5000 µg/ml (w/v) are obtained without regard for the quantity of compounds really solubilised in the solvent. This conventional concentration allows to represent the quantity of dried microalgae effectively required to produce the experimental results described. However, the estimated dry weights of the extracts are reported in Table 1 and the real extract concentration can be calculated. As the composition of the microalgae may change in relation to culture methods and environmental conditions, also the extraction efficacy may change and the extract dry weights have to be considered as raw indications.

Quantity and quality of compounds present in the extracts may vary with respect to both solvent properties and preparation protocol. The selected algae strains showed a different refractoriness to release substances under action of the solvent, basically depending on the characteristics of their respective cell wall. In Table 1, the dry weights of the prepared extracts expressed as percentage of the related integral microalgae material are reported:

TABLE 1

Dry weight of the extracts expressed as percentage of the dry cell material

| Extract code | Chaetoceros calcitrans f. pumilus | Thalassiosira pseudonana | Monodus subterraneus | Chlorococcum minutum |
|---|---|---|---|---|
| Methanol | 54% | 39% | 20% | 24% |
| Ethanol | 22% | 27% | 7-10% | 16% |
| Isopropyl alcohol | 10% | 15% | 6-9% | 10% |
| Ethyl acetate | 9-12% | 18% | 4% | 5-8% |
| Water | 64% | 22% | 26% | 22% |

Extraction Process of Terrestrial Plants

The biological material submitted to extraction can include both epigeal and/or hypogeal parts of the plants. This material can be harvested, rapidly freeze-dried and then finely grinded and extracted following the same process described for microalgae.

However, for the experimental program which led to the present invention, the plants were submitted to extraction freshly harvested. The extraction process consisted of the following steps:

finely grinding parts of the freshly harvested plant using electromechanical devices, blades suitable for manual use or any other methods, homogenizing this minced material pounding it in a mortar together with an extraction solvent selected from the group consisting of $C_1$-$C_4$ aliphatic alcohols, ethyl acetate, water or their mixtures in an amount suitable to effect that the actives move into the solvent phase, optionally at elevated temperatures, removing the dissolved extract from the residue, and recovering the pure extract from the solvent.

Basically, the extracts according to the present invention may be prepared by methods known per se, for example, by aqueous, organic or aqueous/organic extraction of the plants using the solvents explained above. Suitable extraction processes are any conventional extraction processes such as maceration, re-maceration, digestion, agitation maceration, vortex extraction, ultrasonic extraction, counter current extraction, percolation, repercolation, evacolation (extraction under reduced pressure), diacolation and solid/liquid extraction under continuous reflux. Percolation is advantageous for industrial uses. Any size reduction methods known to the expert, for example, freeze grinding, may be used. Preferred solvents for the extraction process are methanol, ethanol, isopropyl alcohol, ethyl acetate and water (preferably hot water with a temperature above 80° C., and more particularly above 95° C.) or mixtures of said organic solvents and water, more particularly, low molecular weight alcohols with more or less high water contents. An extraction with methanol, ethanol and water-containing mixtures thereof is particularly preferred. The extraction process is generally carried out at temperatures of from about 20 to about 100° C., and preferably from about 50 to about 70° C. In one preferred embodiment, the extraction process is carried out in an inert gas atmosphere to avoid the oxidation of the ingredients of the extract. This is particularly important where extraction is carried out at temperatures above 40° C. The extraction times are selected by the expert depending on the starting material, the extraction process, the extraction temperature, and the ratio of solvent to raw material, etc. After the extraction process, the crude extracts obtained may optionally be subjected to other typical steps, such as, for example, purification, concentration and/or decoloration. If desired, the extracts thus prepared may be subjected, for example, to the selective removal of individually unwanted ingredients. The extraction process may be carried out to any degree, but is usually continued to exhaustion. Typical yields (=extracted dry matter based on the quantity of raw fresh material used) in the extraction of the starting materials are of the order of from about 1 to about 20%, preferably from about 1 to about 10%, and more preferably from about 2 to about 6% b.w.—calculated on the starting materials. The extraction is preferably performed on freshly harvested plants, but also frozen or lyophilized material can be used.

In the following, the processes for obtaining the extracts according to the invention is described in more detail:

Water or Methanol or Ethanol or Isopropyl Alcohol or Ethyl Acetate Extraction Process: Single Solvent Extraction Each gram of fresh minced and macerated plant was extracted by treatment with 4 ml of solvent, stirring the suspension at room temperature for 16 hours in the dark;

the residual material was separated from the extract by centrifugation at 2000 G for 15 minutes;

the residual material was washed by suspending it in 0.5 ml of solvent;

the cell material was separated from the washing solvent by centrifugation at 2000 G for 15 minutes;

the residual biomass was washed again by suspending it in 0.5 ml of solvent;

the cell material was separated from the washing solvent by centrifugation at 2000 G for 15 minutes;

the firstly collected extract and the washing solvent volumes were mixed obtaining the final extract, a sample of extract has been evaporated from the solvent in order to weight the dry residual and estimate its concentration.

Extracts can be obtained adopting the protocol above reported also using mixture of the cited solvents. It has to be considered that, working with fresh biomass, alcoholic solvents produce a hydro-alcoholic extract, since the alcoholic solvent determines the extraction of the tissue water over that of the plant components preferentially soluble in alcohol. However, this does not occur in case of solvent immiscible with water, e.g. by using ethyl acetate.

In order to obtain extracts strictly composed by substances selected in base to the affinity for the extractive solvent, it is recommendable to process freeze-dried biomasses.

Differently from what said for the extracts prepared from microalgae, the dry weight of the plant extracts was estimated in order to calculate exactly their concentration in the experimental treatments of the examples hereinafter reported.

Industrial Application

Another object of the present invention is directed at cosmetic and personal care compositions comprising extracts of microalgae or plants and a cosmetically acceptable carrier selected from the group consisting of $C_1$-$C_4$ aliphatic alcohols, polyols having 3 to 12 carbon atoms, oil components, water and their mixtures. Suitable carriers encompass, for example, ethanol, propanol, isopropyl alcohol, all isomeric forms of butanol, ethylene and/or propylene glycol and its dimers and trimers, glycerol, glucose, pentaerythritol and the like. Suitable oil components are disclosed in the following chapter.

The compositions may contain the extracts in amounts of from 0.00001 to 50, preferably from 0.01 to 20, and more preferably from 0.1 to 10% b.w.—the amounts calculated on the dry matter of the extracts. The remaining parts are the carriers. Typically, the administration of the extracts takes place topically; however, it is also possible to use the extracts—especially after encapsulation—for oral uptake.

Cosmetic or Personal Care Composition

Another object of the present invention encompasses a cosmetic or personal care composition comprising said aromatic nitriles and said perfumery grade solvents. The cosmetic or personal care composition may represent a skin care, hair care and/or sun care product, such as for example a cosmetic cream, lotion, spray, emulsion, ointment, gel or mouse and the like. Typical examples are skin creams and hair shampoos, antiperspirants and soaps.

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactants

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:
  products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
  $C_{12/18}$ fatty acid monoesters and diesters of addition products of 1 to 30 mol ethylene oxide onto glycerol;
  glycerol mono- and diesters and sorbitan mono- and diesters of saturated and unsaturated fatty acids containing 6 to 22 carbon atoms and ethylene oxide addition products thereof;
  addition products of 15 to 60 mol ethylene oxide onto castor oil and/or hydrogenated castor oil;
  polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
  addition products of 2 to 15 mol ethylene oxide onto castor oil and/or hydrogenated castor oil;
  partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);
  mono-, di and trialkyl phosphates and mono-, di- and/or tri-PEG-alkyl phosphates and salts thereof;
  wool wax alcohols;
  polysiloxane/polyalkyl polyether copolymers and corresponding derivatives;
  mixed esters of pentaerythritol, fatty acids, citric acid and fatty alcohol and/or mixed esters of $C_{6-22}$ fatty acids, methyl glucose and polyols, preferably glycerol or polyglycerol,
  polyalkylene glycols and
  glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32)® and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric emulsifiers. Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO₃H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan® HMS)
salicylic acid-2-ethylhexyl ester (Neo Heliopan® OS)
triethanolamine salicylate
4-isopropyl benzyl salicylate
anthranilic acid menthyl ester (Neo Heliopan® MA)
diisopropyl cinnamic acid ethyl ester
p-methoxycinnamic acid-2-ethylhexyl ester (Neo Heliopan® AV)
diisopropyl cinnamic acid methyl ester
p-methoxycinnamic acid isoamyl ester (Neo Heliopan® E 1000)
p-methoxycinnamic acid diethanolamine salt
p-methoxycinnamic acid isopropyl ester 2-phenylbenzimidazole sulfonic acid and salts (Neo Heliopan® Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan® MBC)
3-benzylidene-D,L-camphor
N-[(2 and 4)-[2-(oxoborn-3-ylidene) methyl]benzyl] acrylamide polymer
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb® HEB)
benzylidene malonate polysiloxane (Parsol® SLX)
glyceryl ethylhexanoate dimethoxycinnamate
dipropylene glycol salicylate
tris(2-ethylhexyl)-4,4',4"-(1,3,5-triazine-2,4,6-triyltriimino) tribenzoate (=2,4,6-trianilino-(p-carbo-2'-ethylhexyl-1'-oxy)-1,3,5-triazine) (Uvinul® T150).

Broadband filters which are preferably combined with one or more compounds of formula (I) in a preparation according to the present invention are selected from the group consisting of
2-ethylhexyl-2-cyano-3,3-diphenyl acrylate (Neo Heliopan® 303)
ethyl-2-cyano-3,3'-diphenyl acrylate
2-hydroxy-4-methoxybenzophenone (Neo Heliopan® BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl® XL)
2,2'-methylene bis-(6-(2H-benzotriazol-2-yl)-4-1,1,3,3-tetramethylbutyl) phenol) (Tinosorb® M)
2,4-bis-[4-(2-ethylhexyloxy)-2-hydroxyphenyl]-1,3,5-triazine
2,4-bis-[{(4-(2-ethylhexyloxy)-2-hydroxy}phenyl]-6-(4-methoxyphenyl)-1,3,5-triazine (Tinosorb® S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl) phenylamino]-1,3,5-triazine
2,4-bis-[{4-(3-(2-propyloxy)-2-hydroxypropyloxy)-2-hydroxy}phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2"-methylpropyloxy)-2-hydroxy}phenyl]-6-(4-methoxyphenyl)-1,3,5-triazine.

The compositions can comprise further typical detergent and cleansing composition ingredients such as UV-A filters filters which are preferably combined with one or more compounds of formula (I) in a preparation according to the present invention are selected from the group consisting of
4-isopropyl dibenzoyl methane
terephthalylidene dibornane sulfonic acid and salts (Mexoryl® SX)
4-t-butyl-4'-methoxydibenzoyl methane (avobenzone)/(Neo Heliopan® 357)
phenylene bis-benzimidazyl tetrasulfonic acid disodium salt (Neo Heliopan® AP)
2,2'-(1,4-phenylene)-bis-(1H-benzimidazole-4,6-disulfonic acid), monosodium salt
2-(4-diethylamino-2-hydroxybenzoyl) benzoic acid hexyl ester (Uvinul® A Plus)
indanylidene compounds in accordance with DE 100 55 940 A1 (=WO 2002 038537 A1)

The compositions can comprise further typical detergent and cleansing composition ingredients such as UV filters which are more preferably combined with one or more compounds of formula (I) in a preparation according to the present invention are selected from the group consisting of
p-aminobenzoic acid
3-(4'-trimethylammonium) benzylidene bornan-2-one methyl sulfate
salicylic acid homomenthyl ester (Neo Heliopan® HMS)
2-hydroxy-4-methoxybenzophenone (Neo Heliopan® BB)
2-phenylbenzimidazole sulfonic acid (Neo Heliopan® Hydro)
terephthalylidene dibornane sulfonic acid and salts (Mexoryl® SX)
4-tert-butyl-4'-methoxydibenzoyl methane (Neo Heliopan® 357)
3-(4'-sulfo)benzylidene bornan-2-one and salts
2-ethylhexyl-2-cyano-3,3-diphenyl acrylate (Neo Heliopan® 303)
N-[(2 and 4)-[2-(oxoborn-3-ylidene) methyl]benzyl] acrylamide polymer
p-methoxycinnamic acid-2-ethylhexyl ester (Neo Heliopan® AV)
p-aminobenzoic acid ethyl ester (25 mol) ethoxylated (INCI name: PEG-25 PABA)
p-methoxycinnamic acid isoamyl ester (Neo Heliopan® E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl® XL)
4,4'-[(6-[4-(1,1-dimethyl)aminocarbonyl) phenylamino]-1,3,5-triazine-2,4 diyl)diimino]-bis-(benzoic acid-2-ethylhexyl ester) (Uvasorb HEB)
3-(4'-methyl benzylidene)-D,L-camphor (Neo Heliopan® MBC)
3-benzylidene camphor
salicylic acid-2-ethylhexyl ester (Neo Heliopan® OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb® M)
phenylene bis-benzimidazyl tetrasulfonic acid disodium salt (Neo Heliopan® AP)

2,4-bis-[{(4-(2-ethylhexyloxy)-2-hydroxy}phenyl]-6-(4-methoxyphenyl)-1,3,5-triazine
(Tinosorb® S)
benzylidene malonate polysiloxane (Parsol® SLX)
menthyl anthranilate (Neo Heliopan® MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin and/or Hair Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of *rumex* and *ramulus* species, extracts of pine species (*pinus*), extracts of *vitis* species or stilbene derivatives isolated or concentrated therefrom, *saxifrage* extract, *scutelleria* extract, grape extract and/or microalgae extract, in particular *Tetraselmis suecica* Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene derivatives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and analogues thereof, activators of adenylate cyclase and compounds which activate the transfer of melanosomes to keratinocytes such as serine proteases or agonists of the PAR-2 receptor, extracts of plants and plant parts of the *chrysanthemum* species, *sanguisorba* species, walnut extracts, urucum extracts, rhubarb extracts, microalgae extracts, in particular *Isochrysis galbana*, trehalose, erythru-lose and dihydroxyacetone. Flavonoids which bring about skin and hair tinting or browning (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actives

In the context of the invention, anti-ageing or biogenic agents are, for example antioxidants, matrix-metalloproteinase inhibitors (MMPI), skin moisturizing agents, glycosaminglycan stimulators, anti-inflammatory agents, TRPV1 antagonists and plant extracts.

Antioxidants. Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, *sophora, pueraria, pinus, citrus, Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)benzopyran, 3,4-dihydro-6-hydroxy-7-methoxy-2,2-dimethyl-1 (2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and *lentinus edodes* extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan stimulators. Preferred compositions comprise substances stimulating the synthesis of glycosaminoglycans selected from the group consisting of hyaluronic acid and derivatives or salts, Subliskin (Sederma, INCI: Sinorhizobium Meliloti Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalyl-aminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, Sinorhizobium Meliloti Ferment Filtrate, Calcium ketogluconate, *Alpinia galanga* leaf extract and tetradecyl aminobutyroylvalylaminobutyric urea trifluoroacetate.

Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, *Aloe vera*, *Commiphora* species, *Rubia* species, willow, willow-herb, oats, *calendula*, *arnica*, St John's wort, honeysuckle, rosemary, *Passiflora incarnata*, witch hazel, ginger or *Echinacea*; preferably selected from the group consisting of extracts or fractions from camomile, *Aloe vera*, oats, *calendula*, *arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alphabisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide (CO2), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

Desquamating agents. The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-cellulite agents. Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillylnonylamid and derivatives thereof, L-carnitine, coenzyme A, isoflavonoides, soy extracts, ananas extract and conjugated linoleic acid.

Fat enhancing agents. Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxacum*), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, Isochrysis galbana*, licorice, grape, apple, barley or hops or/and hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre.*

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (I-menthoxy)-2-methyl-1,2-propandiol, I-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(−)-isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)-N-(4-Methoxyphenyl)-5-methyl-2-(1-isopropyl)cyclohexane-carboxamide [WS12], oxamates (preferably those described in EP 2033688 A2).

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, ■-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

Capsules and Micro-Capsules

For oral uptake, encapsulation of the extracts represents a preferred embodiment. Usually encapsulation can take place by using gelatine as a matrix. It is also possible to prepare capsules by adding a gelling agent such as, for example, alginate to the extracts and drop the mixture into a bath of a calcium salt. Both methods lead to macro-capsules having a diameter of from about 1 cm to about 5 cm which are toxicologically safe and suitable for consumption.

It may also be desired to encapsulate the extracts for the formulation of compositions which are developed for topical application. This can have different reasons: stabilisation against an interaction with other compounds in the formulation, protection against chemical degradation or simply for the preparation of a very aesthetical product. For this purpose, usually microcapsules are applied. "Microcapsules" are understood to be spherical aggregates with a diameter of from about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third, etc., membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers such as polyacrylates, polyamides, polyvinyl alcohol or polyvinyl pyrrolidone. Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicetin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

Non-Pharmaceutical Applications

In addition, the invention is directed at a number of non-pharmaceutical applications, in particular to the use of the extracts of microalgae or halophytes or psammophilous plants for the treatment of human hair;
for the treatment of human skin;
for the treatment of the human genitals;
for modulating sebogenesis in human hair and/or human skin;
for improving the hair appearance, in particular for treating greasy hair;
for preventing and treating scalp disorders connected with excessive sebogenesesis, in particular for preventing and treating dandruff;
for improving the skin appearance, in particular for treating oily skin;
for preventing and treating skin disorders such as seborrhea, acne vulgaris and comedones;
for modulating the sebogenesis in the human genital area and in particular in the vulva.

All these applications can be summarized under the expression "modulation" of sebogenesis in human skin and hair, in order to fight or prevent symptoms like slight blemishes such as oily skin and greasy hair, and more important dysfunctions such as dandruff, comedones, pimples, pruritus vulvae, etc.

Pharmaceutical Applications

Additional objects of the present invention are related to medicaments, in particular:

An extract of
(i) a microalgae or
(ii) a halophyte or
(iii) a psammophilous plant
for use as a medicament.

Also covered by the present invention is an extract of
(iv) a microalgae or
(v) a halophyte or
(vi) a psammophilous plant
for use as a medicament for preventing or fighting
dysfunctions of human hair and/or skin.
scalp disorders connected with excessive sebogenesis;
dandruff;
seborrhea;
acne vulgaris;
comedones.

In the following, the invention is illustrated by—but not limited to—various working examples.

EXAMPLES

Microalgae

The extraction protocols were selected from many other technical solutions, and they have to be considered as truly exemplificative representations. According to the present invention, freeze-dried biomasses of microalgae were extracted according to the protocol previously described, with a liquid extractant selected from the group consisting of ethyl acetate, isopropanol, ethanol, methanol and water.

The extractant can also comprise a mixture of two or more of the aforementioned solvents.

As already reported, the extract concentrations are expressed here as ratio between the weights of dry biomass extracted and the volume of extractant (µg/ml).

Description of the Experimental Model Based on Ex-Vivo Culture of Human Sebaceous Glands (hSGs) and Subsequent Quantification of their Sebum Content All the reported examples are intended to show the modulation of sebum production exerted by the experimental preparations on human hSGs microdissected and cultivated up to day 6. At the end of the culture time, the sebum is extracted and quantified from each experimental group of hSGs and then normalized by the proteins extracted from the residual hSG material (mg lipids/mg proteins). As a result, the biological activity of the tested compounds is inferred by comparing the ratio lipids/proteins of the treated glands with that of the control group.

Organ Culture Technique

Using micro-scissors and tweezers, hSGs were isolated from the pilosebaceous units of a scalp skin sample. They were seeded in 24-well plates at the density of 8 hSGs/well and then cultivated in 500 µl of modified William E medium. After 24 hours of culture the viability of the hSGs was assessed by means of resazurine assay. Briefly, each hSGs group was transferred onto a microplate well with 200 µl of 10% resazurin culture medium for 2 hours. During this period the resazurin, a non-fluorescent blue dye, is reduced by living cells to the pink coloured and highly red fluorescent resorufin. At the end of the incubation, the medium was withdrawn and analyzed for the resazurin fluorescence in a plate reader (Em. 570 nm-Ex. 590 nm). The fluorescence signal positively correlates with the hSGs viability. Since the resazurin test is not toxic, the hSGs were then seeded in a 24-well plate and cultivated with the experimental culture media in order to start the treatments. The control received William E medium appropriately modified, while the samples submitted to experimental treatments received the same medium supplemented with experimental extracts. The culture medium was renewed every other day. After six days of organ culture, the viability of the hSGs was again assessed via resazurine assay and then, having attested their good viability, each group of hGSs was collected and analyzed for quantifying the sebum content.

Analysis of the Sebum Content

In order to make the estimated productivity of the glands comparable, which are variable in biomass, their total sebum content was estimated and divided by the proteins extracted from the gland tissue, obtaining the ratio between the produced sebum and the tissue proteins (i.e. mg of lipids/mg of proteins).

The sebum extraction and quantification was performed as reported below:

Each hSG group was homogenized in 100 µl of isopropyl alcohol;

the sample was centrifuged at 14,000 G for 5 minutes and then the supernatant (containing the extracted sebum) was collected;

the sebum extract was analyzed in triplicate with a Direct Detect IR Spectrometer (Millipore), which provided the total lipid concentration of the supernatant (mg/ml);

the total lipids of the hSGs was quantified multiplying the supernatant lipid concentration (indention 3) by the volume of isopropyl alcohol adopted for the lipid extraction (indention 1);

the pellet remaining from indention 2 was dried by means of a vacuum dry evaporator and then again homogenized in 50 µl of proteolytic buffer (20 mM Tris/HCl pH 7.5, 150 mM NaCl, 2 mM EDTA, 0.5% Triton X-100, 2 mM DTT, 1% protease inhibitor cocktail);

after an appropriate incubation time, this extractive mixture was centrifuged at 14,000 G for 10 minutes and the supernatant was collected and analyzed in triplicate with a Direct Detect IR Spectrometer (Millipore);

the obtained total protein concentration was multiplied by the extractive volume (indention 5) in order to quantify the total proteins of the hSGs;

the total lipid amount (indention 4), i.e. the amount of sebum, was divided by the total proteins (indention 7) in order to obtain the normalized amount of lipids per mg of proteins (mg of lipids/mg of proteins).

The amounts of normalized lipids obtained from the treated groups, i.e. the sebum produced by each group of hSGs, were expressed in percentages with respect to the value obtained in the control group, in order to point out the regulatory effect performed by the experimental treatment.

Examples 1 to 6

Activity of Ethanolic and Aqueous Extracts of *Thalassiosira* on Human Sebaceous Glands (hSGs)

hSGs were taken from a scalp sample and cultivated as previously described. Ethanolic and aqueous extracts obtained from *Thalassiosira pseudonana* were vacuum dried and then dissolved in DMSO at the final concentration 10,000 µg/ml. The experimental culture media were supplemented with 1 µl/ml of these stock solutions in order to obtain the experimental treatments at 10 µg/ml, while the lower concentrations were obtained from these supplemented media by serial volumetric dilution 1:10 with standard medium. All the treatments were supplemented with DMSO, whenever needed, to the final concentration of 1 µl/ml. The control group was cultured in standard medium supplemented with 1 µl/ml of DMSO. As positive control, a 5 µM Capsaicin treatment was included in the experimental design. Capsaicin is an active component of chili peppers suitable to inhibit sebogenesis [Tóth et al., *J. Invest. Derm.* (2009), 129: 329-339]. The results obtained from the experiments are reported in Table 2.

TABLE 2

Sebum content in hSGs following treatment with *Thalassiosira* extracts. Responses are expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 1.4 | |
| 0 | capsaicin | 5 µM | 90.3 | 1.8 | p < 0.01 |
| 1 | EtOH | 0.1 µg/ml | 50.2 | 1.3 | p < 0.01 |

TABLE 2-continued

Sebum content in hSGs following treatment with *Thalassiosira* extracts. Responses are expressed as % ratio of the control group performance. The capsaicin treatment was included as positive control. The statistical significance was evaluated by means of one-way ANOVA Permutation test with Dunnett permutation post-hoc test

| Example | Sample | Amount | Average | Std. error | Statistics |
|---|---|---|---|---|---|
| 2 | EtOH | 1.0 µg/ml | 78.6 | 2.0 | p < 0.01 |
| 3 | EtOH | 10.0 µg/ml | 49.2 | 1.6 | p < 0.01 |
| 4 | Water | 0.1 µg/ml | 51.8 | 1.1 | p < 0.01 |
| 5 | Water | 1.0 µg/ml | 50.4 | 1.1 | p < 0.01 |
| 6 | Water | 10.0 µg/ml | 68.0 | 1.0 | p < 0.01 |

The positive control treatment reduced the sebum content of the hSGs by 10% in comparison with the control group. However, surprisingly, both the *Thalassiosira* extracts produced an intense inhibition of the sebogenesis, ranging from 32% to 51% in comparison with the control group.

All these results are highly significant on a statistical basis.

Examples 7 to 8

Activity of Ethanolic and Aqueous Extracts of *Thalassiosira* on Human Sebaceous Glands (hSGs)

The ethanolic and aqueous extracts tested in the previous experiment were again tested at the single concentration of 0.1 µg/ml. No positive control was included in this experimental design. The results are reported in Table 3:

TABLE 3

Sebum content in hSGs following treatment with *Thalassiosira* extracts. Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 2.0 | |
| 7 | EtOH | 0.1 µg/ml | 84.6 | 2.2 | p < 0.01 |
| 8 | Water | 0.1 µg/ml | 65.5 | 1.3 | p < 0.01 |

The results confirmed the intense inhibition of sebum production induced by the treatments with extracts of *Thalassiosira*. In this case, at the tested concentration, the aqueous extract produced a more intense inhibition than the ethanolic one.

Examples 9 to 13

Activity of Various *Thalassiosira* Extracts on Human Sebaceous Glands (hSGs)

The previously described experimental protocol was used to study the activity of some extracts obtained from *Thalassiosira pseudonana* by means of different solvents: ethyl acetate (EtAc), ethanol (EtOH) and water. The biological activity of these preparations was compared by treating groups of hSGs microdissected from a single sample of scalp.

Organ culture and supplementation of the culture media were performed as reported for the previous experiments. This experimental design included two different positive controls selected from among commercial compounds active on sebogenesis: 5α-Avocuta (Butyl-Avocadate), which is an active ingredient derived from avocado pears, and Asebiol™, a commercial active product formulated combining aminoacids, sulphated peptides, vitamin B complex and allantoin.

The variations of sebum content expressed by each group in comparison to the control are reported in Table 4.

TABLE 4

Sebum content in hSGs following treatment with *Thalassiosira* extracts obtained with ethyl acetate (EtAc), ethanol (EtOH) and water (Water). 5α-Avocuta (Butyl-Avocadate) and Asebiol ™ were included as positive controls. Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control (DMSO) | 0 | 100.0 | 1.0 | |
| 0 | 5α-Avocuta | 0.1% | 82.4 | 1.6 | P < 0.01 |
| 0 | Asebiol ™ | 0.1% | 82.4 | 2.7 | P < 0.01 |
| 9 | EtAc | 0.1 µg/ml | 92.2 | 1.3 | P < 0.05 |
| 10 | EtAc | 1.0 µg/ml | 77.1 | 0.6 | P < 0.01 |
| 11 | EtOH | 0.1 µg/ml | 87.1 | 2.3 | P < 0.01 |
| 12 | EtOH | 1.0 µg/ml | 80.5 | 1.3 | P < 0.01 |
| 13 | Water | 0.1 µg/ml | 81.4 | 2.0 | P < 0.01 |

The results obtained attest that all the experimental preparations inhibited the production of sebum in measures comparable to or higher than the positive controls. In fact, the sebum content of the hSGs treated with *Thalassiosira* extracts was from 7.8% to 22.9% lower than the control group, while both the commercial products reduced the sebum content by 17.6%. All the extracts produced significant (P<0.05) or very significant (P<0.01) inhibitions on a statistical basis.

Examples 14 to 19

Activity on Human Sebaceous Glands (hSGs) of Ethanolic Extracts Obtained from Microalgae Belonging to the Genera *Chlorococcum, Chaetoceros* and *Monodus*

The experimental protocol previously described was adopted to study the activity of ethanolic extracts obtained from microalgae belonging to the genera *Chlorococcum* (C), *Chaetoceros* (K) and *Monodus* (M). For the present example, in particular, the ethanolic extracts (EtOH) were prepared from *Chorococcum minutum, Chaetoceros calcitrans f. pumilus* and *Monodus subterraneus*. A culture medium supplemented with 5 µM capsaicin was included in the experimental design as positive control.

After 6 days of culture and 5 of treatment, as previously described, the sebum content was estimated in each group of hSGs and the detected variations in comparison to the control are reported in Table 5.

TABLE 5

Sebum content in hSGs following treatment with ethanolic extracts (EtOH) obtained from *Cholorococcum minutum* (C), *Chaetoceros calcitrans f. pumilus* (K) and *Monodus subterraneus* (M). Capsaicin treatment was included as positive control. Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control (DMSO) | 0 | 100.0 | 1.7 | |
| 0 | Capsaicin | 0 | 68.5 | 1.5 | P < 0.01 |
| 14 | K - EtOH | 0.1 µg/ml | 60.6 | 2.3 | P < 0.01 |
| 15 | K - EtOH | 10 µg/ml | 59.3 | 1.2 | P < 0.01 |
| 16 | M - EtOH | 0.1 µg/m | 71.3 | 2.3 | P < 0.01 |
| 17 | M - EtOH | 10 µg/ml | 65.4 | 1.3 | P < 0.01 |
| 18 | C - EtOH | 0.1 µg/ml | 54.1 | 1.0 | P < 0.01 |
| 19 | C - EtOH | 10 µg/ml | 53.6 | 0.3 | P < 0.01 |

The results, surprisingly, attest that the screened microalgal extracts exert a significant inhibitory action on the sebum production by hSGs, generally more intense than that shown by the positive control (Capsaicin). All the extracts produced a reduction in sebum content ranging between 29% (*Monodus* 0.1 µg/ml) and 46% (*Chlorococcum* 0.1-10 µg/ml). All the detected responses are highly significant on a statistical basis.

Examples 20 to 25

Activity on Human Sebaceous Glands (hSGs) of Ethanolic Extracts Obtained from Microalgae Belonging to the Genera *Chlorococcum, Chaetoceros* and *Monodus*

The previous experiment was replicated with hSGs taken from a different donor. The results are reported in Table 6:

TABLE 6

Sebum content in hSGs following treatment with ethanolic extracts (EtOH) obtained from *Cholorococcum minutum* (C), *Chaetoceros calcitrans f. pumilus* (K) and *Monodus subterraneus* (M). Capsaicin treatment was included as positive controls. Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control (DMSO) | 0 | 100.0 | 1.1 | |
| 0 | Capsaicin | 0 | 59.2 | 0.7 | P < 0.01 |
| 20 | K - EtOH | 0.1 µg/ml | 58.0 | 1.2 | P < 0.01 |
| 21 | K - EtOH | 10 µg/ml | 59.2 | 0.9 | P < 0.01 |
| 22 | M - EtOH | 0.1 µg/ml | 67.9 | 0.9 | P < 0.01 |
| 23 | M - EtOH | 10 µg/ml | 52.8 | 0.6 | P < 0.01 |
| 24 | C - EtOH | 0.1 µg/ml | 56.1 | 0.5 | P < 0.01 |
| 25 | C - EtOH | 10 µg/ml | 64.8 | 0.9 | P < 0.01 |

The results confirmed the intense inhibiting activity of the experimental extracts on sebogenesis. All the extracts produced a reduction in sebum content ranging between 32% (*Monodus* 0.1 µg/ml) and 47% (*Monodus* 10 µg/ml). All the detected responses are highly significant on a statistical basis.

Examples 26 to 29

Activity on Human Sebaceous Glands (hSGs) of Aqueous Extracts Obtained from Microalgae Belonging to the Genera *Monodus* and *Chaetoceros*

The protocol used for the previous experiment was adopted for screening the biological activity of aqueous extracts obtained from *Monodus subterraneous* and *Chorococcum minutum*. In this case, the concentrated aqueous extracts were used directly to supplement the experimental culture media, without the addition of DMSO as intermediate vehicle. The treatment results are reported in Table 7:

TABLE 7

Sebum content in hSGs following treatment with aqueous extracts (water) obtained from *Monodus subterraneous* (M) and *Chlorococcum minutum* (C). Capsaicin treatment was included as positive control. Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control (DMSO) | 0 | 100.0 | 0.9 | |
| 0 | Capsaicin | 0 | 97.4 | 1.0 | n.s. |
| 26 | M - water | 0.1 µg/ml | 95.8 | 1.3 | P < 0.05 |

TABLE 7-continued

Sebum content in hSGs following treatment with aqueous extracts (water) obtained from *Monodus subterraneous* (M) and *Chlorococcum minutum* (C). Capsaicin treatment was included as positive control. Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 27 | M - water | 10 µg/ml | 91.2 | 0.8 | $P < 0.01$ |
| 28 | C - water | 0.1 µg/ml | 91.3 | 1.1 | $P < 0.01$ |
| 29 | C - water | 10 µg/ml | 80.2 | 1.2 | $P < 0.01$ |

The aqueous extracts resulted suitable to inhibit the sebum production by hSGs. The tested donor resulted poorly responsive, as attested by the low inhibition produced by the treatment with the positive control (−3%). Nevertheless, all the experimental preparations inhibited the sebum production in a statistically significant ($P<0.05$) or very significant ($P>0.01$) measure.

B. Terrestrial Plants

As for microalgae, the extraction protocols were selected from many other technical solutions, and have to be considered as purely exemplificative representations. According to the present invention, freshly harvested plants were minced and extracted with a liquid extractant selected from the group consisting of ethyl acetate, isopropanol, ethanol, methanol and water. The extractant can also comprise a mixture of two or more of these solvents.

In the following examples, differently from the conventional concentration adopted for the microalgae extracts, the extract concentration was expressed as actual content of dry weight per volume unit.

Examples 30 to 31

Activity on Human Sebaceous Glands (hSGs) of Water Extract Obtained from Psammophilous Plants Belonging to the Genus *Echinophora*.

The previously described experimental protocol was adopted to study the activity of the aqueous extract obtained from plants belonging to the genus *Echinophora*. For the present example, in particular, the aqueous extract was prepared from *Echinophora spinosa* (ES), a typical plant growing on sand dunes along the Mediterranean coasts. A culture medium supplemented with 5 µM capsaicin was included in the experimental design as positive control.

After 6 days of culture and 5 of treatment, as previously described, the sebum content was estimated in each group of hSGs and the results are reported in Table 6.

TABLE 8

Sebum content in hSGs following treatment with aqueous extract (water) obtained from *Echinophora spinosa* (ES). Capsaicin treatment was included as positive control. Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 1.8 | |
| 0 | Capsaicin | 0 | 91.9 | 1.5 | $P < 0.05$ |
| 30 | ES - water | 0.1 µg/ml | 82.8 | 1.2 | $P < 0.01$ |
| 31 | ES - water | 10 µg/ml | 87.5 | 1.8 | $P < 0.01$ |

The aqueous extract obtained from *Echinophora spinosa* inhibited the sebum production by 13.2-17.5%, i.e. 1.5-2 fold the inhibition induced by the positive control. This effect has to be regarded as very significant based on the statistical analysis used.

Examples 32 to 40

Activity on Human Sebaceous Glands (hSGs) of Various Extracts Obtained from Plants Belonging to the Genera *Echinophora*, *Inula*, *Sarcocornia* and *Salicornia*.

The previously described experimental protocol was adopted to study the activity of the extracts obtained from plants belonging to the genera *Echinophora*, *Inula*, *Sarcocornia* and *Salicornia*. For the present example, an ethanolic extract was prepared from the psammophilous plant *Echinophora spinosa* (ES), whereas ethanolic and aqueous extracts were prepared from *Inula chritmoides* (IC), a typical plant growing on sand dunes as well as in salty soils. Methanolic extracts were also prepared from two halophytes typical of Mediterranean salt marshes: *Sarcocornia fruticosa* (SF) and *Salicornia veneta* (SV).

After 6 days of culture and 5 of treatment, as previously described, the sebum content was estimated in each group of hSGs and the results are reported in Table 9.

TABLE 9

Sebum content in hSGs following treatment with ethanolic extract (EtOH) and aqueous extract (water) obtained from *Inula chritmoides* (IC) and *Echinophora spinosa* (ES), methanolic extracts (MeOH) obtained from *Sarcocornia fruticosa* (SF) and *Salicornia veneta* (SV). Capsaicin treatment was included as positive control. Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 3.1 | |
| 32 | ES - EtOH | 0.1 µg/ml | 114.0 | 2.9 | $P < 0.01$ |
| 33 | ES - EtOH | 10 µg/ml | 101.9 | 2.9 | n.s. |
| 34 | IC - EtOH | 10 µg/ml | 71.8 | 1.1 | $P < 0.01$ |
| 35 | IC - water | 0.1 µg/ml | 87.5 | 1.9 | $P < 0.01$ |
| 36 | IC - water | 10 µg/ml | 80.3 | 1.4 | $P < 0.01$ |
| 37 | SF - MeOH | 0.1 µg/ml | 86.3 | 1.0 | $P < 0.01$ |
| 38 | SF - MeOH | 10 µg/ml | 76.1 | 1.9 | $P < 0.01$ |
| 39 | SV - MeOH | 0.1 µg/ml | 78.8 | 1.3 | $P < 0.01$ |
| 40 | SV - MeOH | 10 µg/ml | 73.6 | 1.6 | $P < 0.01$ |

Most of the treatments produced a significant decrease of sebum production, ranging between −13% and −28% in comparison with the control group. These effects are very significant based on the statistical analysis used. Interestingly, the ethanolic extract of *Echinophora* produced a significant stimulation of sebogenesis at 0.1 µg/ml. Since the water extract of this plant produced a sebum decrease (see examples 30-31), it is assumable that the stimulating active is a lipophilic compound.

Examples 41 to 44

Activity on Human Sebaceous Glands (hSGs) of Ethanol Extracts Obtained from *Sarcocornia* and *Salicornia*.

The previously described experimental protocol was adopted to study the activity of the ethanolic extracts obtained from plants belonging to the genera *Sarcocornia* and *Salicornia*. For the present experiment, *Sarcocornia fruticosa* (SF) and *Salicornia veneta* (SV) were selected as exemplificative species.

After 6 days of culture and 5 of treatment, as previously described, the sebum content was estimated in each group of hSGs and the results are reported in Table 10.

TABLE 10

Sebum content in hSGs following treatment with ethanolic extract (EtOH) obtained from *Sarcocomia fruticosa* (SF) and *Salicomia veneta* (SV). Capsaicin treatment was included as positive control. Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 0.8 | |
| 0 | Capsaicin | 5 µg/ml | 62.9 | 0.4 | $P < 0.01$ |
| 41 | SF - EtOH | 0.1 µg/ml | 91.8 | 1.2 | $P < 0.01$ |
| 42 | SF - EtOH | 10 µg/ml | 83.1 | 1.0 | $P < 0.01$ |
| 43 | SV - EtOH | 0.1 µg/ml | 60.4 | 0.3 | $P < 0.01$ |
| 44 | SV - EtOH | 10 µg/ml | 92.3 | 0.8 | $P < 0.01$ |

All the treatments produced a significant decrease of sebum production, ranging between −8% and −40% in comparison with the control group. These effects are very significant based on the statistical analysis used.

Examples 45 to 53

Activity on Human Sebaceous Glands (hSGs) of Various Extracts Obtained from *Sarcocornia*, *Salicornia*, *Echinophora* and *Chaetoceros*.

The previously described experimental protocol was adopted to study the activity of the aqueous and ethanolic extracts obtained from the following plants and microalgae selected as exemplificative species: *Sarcocornia fruticosa* (SF), *Salicornia veneta* (SV), *Echinophora spinosa* (ES) and *Chaetoceros calcitrans* (K).

After 6 days of culture and 5 of treatment, as previously described, the sebum content was estimated in each group of hSGs and the results are reported in Table 11.

TABLE 11

Sebum content in hSGs following treatment with ethanolic (EtOH) or aqueous (water) extracts obtained from *Sarcocomia fruticosa* (SF), *Salicomia veneta* (SV), *Echinophora spinosa* (ES) and *Chaetoceros calcitrans* (K). Responses are expressed as % ratio of the control group performance. The statistical significance was evaluated by means of one-way ANOVA Permutation test with Dunnett permutation post-hoc test

| Example | Sample | Amount | Average | Std. error | Statistics |
|---|---|---|---|---|---|
| 0 | Control | 0 | 100.0 | 1.4 | |
| 0 | SF - water | 0.1 µg/ml | 116.7 | 4.3 | $P < 0.01$ |
| 45 | SF - water | 10 µg/ml | 106.6 | 3.4 | n.s. |
| 46 | SV - water | 0.1 µg/ml | 88.1 | 2.8 | $P < 0.05$ |
| 47 | SV - water | 10 µg/ml | 95.4 | 2.3 | n.s. |
| 48 | SV - EtOH | 0.1 µg/ml | 81.8 | 1.4 | $P < 0.01$ |
| 49 | SV - EtOH | 10 µg/ml | 83.7 | 1.5 | $P < 0.01$ |
| 50 | ES - EtOH | 0.1 µg/ml | 155.6 | 5.3 | $P < 0.01$ |
| 51 | ES - EtOH | 10 µg/ml | 123.8 | 1.3 | $P < 0.01$ |
| 52 | K - water | 0.1 µg/ml | 132.2 | 2.5 | $P < 0.01$ |
| 53 | K - water | 10 µg/ml | 106.9 | 2.4 | n.s. |

All the treatments produced significant responses, at least for one of the two tested concentrations. Both the acqueous and ethanolic extracts obtained from *Salicornia veneta* inhibited the sebum production, whereas all the other extracts induced the opposite response, i.e. stimulated the sebum production. These data attest that from *Sarcocornia fruticosa*, *Echinophora spinosa* and *Chaetoceros calcitrans*, it is possible to obtain extracts with opposite effects depending on the solvent adopted for the extract preparation.

CONCLUSIVE REMARKS

The reported examples attest that the selected microalgae, halophytes and psammophilous plants are suitable sources of natural extracts for the regulation of sebum production. Their biological activity was shown to be comparable to or higher than that of some positive controls selected from among the well-known sebum-inhibitors (i.e. 5α-Avocuta, Asebiol™, Capsaicin).

The described results support the proposed uses of the extracts to treat skin, hair and genitals, in order to prevent and/or treat the excessive secretion of sebum and the related aesthetic problems or skin disorders (greasy hair and skin, dandruff, acne, discomfort of the vulval region etc.).

What claimed is:

1. A method for making and using an extract of microalgae comprising the steps of
   (a) contacting each gram of plant material, optionally minced or crushed or micronized, with 4 ml of a solvent selected from the group consisting of $C_1$-$C_4$ aliphatic alcohols, ethyl acetate, water and mixtures thereof, and causing active agent in the plant material to move into the solvent phase, optionally at elevated temperatures,
   (b) removing the dissolved extract from the residue,
   (c) recovering the extract from the solvent, and
   (d) topically or orally administering the extract of microalgae for the regulation of sebum production by sebaceous glands to a patient in need of scalp treatment, treatment for greasy hair, dandruff treatment, treatment for seborrheic dermatitis, treatment of oily skin, treatment for comedones, and treatment of external female genitalia thereof, wherein the extract of microalgae belongs to the genus *Chaetoceros*, *Chlorococcum*, *Thalassiosira*, or *Monodus*.

2. The method according to claim 1, additionally comprising combining the extract with a cosmetically acceptable carrier selected from the group consisting of $C_1$-$C_4$ aliphatic alcohols, polyols having 3 to 12 carbon atoms, oil components, water and mixtures thereof.

3. The method according to claim 1, comprising additionally preventing and treating acne with the extract of microalgae.

4. The method according to claim 1, wherein the microalgae is Bacillariophyceae belonging to the genus of *Chaetoceros* and *Thalassiosira*.

5. The method according to claim 4, wherein the microalgae belongs to the genus of *Chaetoceros*.

* * * * *